(12) United States Patent
Pezzuto et al.

(10) Patent No.: US 6,569,842 B2
(45) Date of Patent: May 27, 2003

(54) METHOD OF PREPARING AND USE OF PRODRUGS OF BETULINIC ACID DERIVATIVES

(75) Inventors: John M. Pezzuto, River Forest, IL (US); Jerome W. Kosmeder, II, Oak Park, IL (US); Ze-Qi Xu, Naperville, IL (US); Nian En Zhou, Naperville, IL (US); Miriam Elaine Goldsmith, Naperville, IL (US)

(73) Assignee: Board of Trustees of the University of Illinois, The, Urbana, IL (US)

( * ) Notice: Subject to any disclaimer, the term of this patent is extended or adjusted under 35 U.S.C. 154(b) by 0 days.

(21) Appl. No.: 09/930,656

(22) Filed: Aug. 15, 2001

(65) Prior Publication Data

US 2002/0052352 A1 May 2, 2002

Related U.S. Application Data

(60) Provisional application No. 60/226,536, filed on Aug. 16, 2000.

(51) Int. Cl.⁷ .......................... A61K 31/56; C07J 53/00
(52) U.S. Cl. ....................................... 514/169; 552/510
(58) Field of Search ........................... 514/169; 552/510

(56) References Cited

U.S. PATENT DOCUMENTS

| | | | |
|---|---|---|---|
| 5,658,947 A | 8/1997 | DasGupta et al. | 514/510 |
| 5,804,575 A | 9/1998 | Pezzuto et al. | 514/169 |
| 5,869,535 A | 2/1999 | Pezzuto et al. | 514/640 |
| 5,962,527 A | 10/1999 | Pezzuto et al. | 514/569 |
| 6,225,353 B1 | 5/2001 | Pezzuto et al. | 514/640 |

FOREIGN PATENT DOCUMENTS

| | | | |
|---|---|---|---|
| EP | 0 943 620 | 9/1999 | C07J/63/00 |
| WO | WO 93/10142 | 5/1993 | C07J/63/00 |
| WO | WO 94/26725 | 11/1994 | C07D/257/04 |
| WO | WO 00/59492 | 10/2000 | A61K/31/00 |

OTHER PUBLICATIONS

Fujioka et al., *Journal of Natural Products*, vol. 57, No. 2, pp. 243–247, Feb. 1994.
Sun et al., *J. Med. Chem.*, 41, pp. 4648–4657 (1998).
Yasukawa et al., *Phytomedicine*, vol. 4, pp. 309–313 (1995).
Macias et al., *J. Chem. Col.*, 23(7), pp. 1781–1803 (1997), abstract only.
Pradhan et al., *Indian J. Chem.*, Sect. B: Org. Chem. Incl. Med. Chem, 34B(6), pp. 540–542 (1995), abstract only.
Dina et al., *Indian J. Chem.*, Sect. B: Org. Chem. Incl. Med. Chem, 34B(7), pp. 624–628 (1995), abstract only.
Patra et al., *Indian J. Chem., Sect. B*, 27B(2), pp. 170–172 (1988), abstract only.
Tanaka et al., *J. Nat. Prod.*, 63(1), pp. 99–103 (2000), abstract only.
Kuo et al., *Chin. Pharm. J.*, 49(4), pp. 207–216 (1997), abstract only.
Evers et al., *J. Med. Chem.*, 39, pp. 1056–1068 (1996).
Mayaux et al., *Proc. Natl. Acad. Sci., USA*, vol. 91, pp. 3564–3568, Apr. 1994.
Fang et al., *Phytochemistry*, 23(3), pp. 631–633 (1984), abstract only.
Hashimoto et al., *Bioorganic & Medicinal Chemistry*, vol. 5, No. 12, pp. 2133–2143 (1997).
Ma et al., *Chem. Pharm. Bull.* 47(2), pp. 141–145 (1999).
Kim et al., *Bioorganic & Medicinal Chemistry Letters*, 8(13), pp. 1707–1712 (1998).
Noda et al., *Chem. Pharm. Bull.*, 45(10), pp. 1665–1670 (1997).
Kitajima et al., *Chem. Pharm. Bull.*, 38(3), pp. 714–716 (1990).
Kashiwada et al., *J. Med. Chem.*, 39, pp. 1016–1017 (1996).

*Primary Examiner*—Barbara P. Badio

(57) ABSTRACT

A composition and method of preventing or inhibiting tumor growth and, more particularly, of treating a malignant tumor, using prodrugs of plant-derived compounds and derivatives is disclosed. In the method, a composition containing betulinic acid or a betulinic acid derivative is administered in a prodrug form to release betulinic acid or a betulinic acid derivative in vivo at the tumor site.

7 Claims, No Drawings

METHOD OF PREPARING AND USE OF PRODRUGS OF BETULINIC ACID DERIVATIVES

CROSS REFERENCE TO RELATED APPLICATION

This application claims the benefit of U.S. provisional patent application No. 60/226,536, filed Aug. 16, 2000.

FIELD OF THE INVENTION

The present invention relates to compositions and methods of inhibiting tumors and, more particularly, of treating a malignant tumor, like a melanoma, using plant-derived compounds and derivatives thereof, and in particular, prodrugs of betulinic acid and betulinic acid derivatives.

BACKGROUND OF THE INVENTION

Over the past four decades the incidence of melanoma has been increasing at a higher rate than any other type of cancer. It is now theorized that one in ninety American Caucasians will develop malignant melanoma in their lifetime. While an increasing proportion of melanomas are diagnosed sufficiently early to respond to surgical treatment and achieve a greater than 90% ten-year survival rate, it is estimated that nearly 7,000 individuals suffering from metastatic melanoma will die in the United States each year.

For patients afflicted with a metastatic melanoma not amenable to surgical extirpation, treatment options are limited. 5-(3,3-Dimethyl-1-triazenyl)-1-H-imidazole-4-carboxamide (dacarbazine, DTIC) is the most efficacious single chemotherapeutic agent for melanoma having an overall response rate of 24%. But the duration of response to DTIC is generally quite poor. Combination therapy with other synthetic and recombinant agents, including N,N'-bis (2-chloroethyl)-N-nitrosurea (carmustine, BCNU), cisplatin, tamoxifen, interferon-alpha (INF-$\alpha$), and interleukin-2 (IL-2), has a higher response rate (e.g., 30–50%) in some trials, but a durable complete response rate is uncommon and toxicity is increased. Sequential chemotherapy also has promise, but current treatment options for individuals suffering from metastatic melanoma are unsatisfactory.

Various drugs derived from natural products, such as adriamycin (doxorubicin), bleomycin, etoposide, and vincristine, and their derivatives, have been tested for efficacy against melanoma either as single agents or in combination therapy. However, similar to the synthetic and recombinant compounds, these compounds exhibit low response rates, transient complete responses, and high toxicities.

Nonetheless, as demonstrated by known and presently used cancer chemotherapeutic agents, plant-derived natural products are a proven source of effective drugs. Two such useful natural product drugs are paclitaxel (taxol) and camptothecin. Paclitaxel, originally derived from the bark of the Pacific yew tree *Taxus brevifolia* Nutt. (Taxaceae), currently is used for the treatment of refractory or residual ovarian cancer. More recently, clinical trials have investigated the possible role of paclitaxel in the treatment of metastatic melanoma. As a single agent, taxol displays activity comparable to cisplatin and IL-2. Taxol functions by a unique mode of action, and promotes the polymerization of tubulin. Thus, the antitumor response mediated by taxol is due to its antimitotic activity.

The second drug of prominence, camptothecin, was isolated from the stem bark of a Chinese tree, *Camptotheca acuminata* Decaisne (Nyssaceae). Camptothecin also functions by a novel mechanism of action, i.e., the inhibition of topoisomerase I. Phase II trials of a water-soluble camptothecin prodrug analog, irinotican (CPT-11), have been completed in Japan against a variety of tumors with response rates ranging from 0% (lymphoma) to 50% (small cell lung). Topotecan, another water-soluble camptothecin analog, currently is undergoing Phase II clinical trials in the United States.

In addition, studies have shown that betulinic acid, and betulinic acid derivatives, can inhibit other types of cancer cells, such as neuroblastoma, in addition to melanoma. For example, Das Gupta et al. U.S. Pat. No. 5,658,947 discloses that betulinic acid is useful for the selective control or treatment of human melanoma, and Pezzuto et al. U.S. Pat. No. 5,962,527 discloses the selective activity of derivatives of betulinic acid against melanoma cells.

However, a disadvantage associated with the use of betulinic acid or a betulinic acid derivative in the treatment of a cancer is the problem encountered in formulating these active drugs and in providing suitable dosage forms for the treatment of various cancers. The present application is directed to overcoming this disadvantage and providing useful prodrugs of betulinic acid and derivatives thereof that are easy to formulate into a variety of dosage forms and that release betulinic acid or the derivative thereof in vivo.

SUMMARY OF THE INVENTION

The present invention is directed to a method and composition for preventing or inhibiting tumor growth. The active compound is a prodrug of betulinic acid or a betulinic acid derivative which generates betulinic acid or a derivative thereof in vivo. Betulinic acid is a natural product obtained by a method comprising the steps of preparing an extract from the stem bark of *Ziziphus mauritiana* and isolating the betulinic acid. Alternatively, betulin can be isolated from the extract, and betulinic acid then is prepared from betulin by a series of synthetic steps.

Betulinic acid can be isolated from the extract by mediating a selective cytotoxic profile against human melanoma in a subject panel of human cancer cell lines, conducting a bioassay-directed fractionation based on the profile of biological activity using cultured human melanoma cells (MEL-2) as the monitor, and obtaining betulinic acid therefrom as the active compound. The resulting betulinic acid can be used to prevent or inhibit tumor growth, or can be converted to a derivative to prevent or inhibit tumor growth.

The physiochemical properties of betulinic acid, e.g., a high melting point and limited solubility in hydrophilic and hydrophobic solvents, make it difficult to produce betulinic acid-containing pharmacological formulations. The present invention is directed to providing betulinic acid or a betulinic acid derivative in a form that is easy to formulate and wherein endogenous enzymes can release the active betulinic acid or derivative in vivo.

Therefore, an important aspect of the present invention is to provide a method and composition for preventing or inhibiting tumor growth and, particularly, for preventing or inhibiting the growth of a malignant tumor using a natural product-derived compound, or a derivative thereof, in an easy-to-formulate form.

Another aspect of the present invention is to improve the bioavailability of betulinic acid and betulinic acid derivatives in an individual by administering a therapeutically effective amount of a prodrug of betulinic acid or betulinic acid derivative to an individual in need thereof.

Another aspect of the present invention is to provide a treatment method utilizing a prodrug of betulinic acid or derivative thereof to prevent the growth or spread of cancer cells, wherein betulinic acid or a derivative thereof is administered to an individual in need thereof in a manner consistent with the treatment of a cancer sensitive to betulinic acid or a derivative thereof, e.g., in a topical preparation for the prevention, inhibition, or treatment of melanoma, or intravenously or intraperitoneally for other forms of cancer.

Yet another aspect of the present invention is to overcome the problem of high mammalian toxicity associated with synthetic anticancer agents by using a natural product-derived compound, e.g., a prodrug of betulinic acid or a betulinic acid derivative.

Yet another aspect of the present invention is to provide a composition and method of treating various forms of cancer with a naturally occurring product, or a derivative thereof. In particular, the present invention is directed to inhibiting malignant tumor growth associated with melanoma, neuroblastoma, breast cancer, lung cancer, fibrosarcoma, colon cancer, oral epidermoid carcinoma, epidermoid carcinoma, prostate cancer, hormone-dependent breast cancer, and glioma.

In particular, an aspect of the prevent invention is to provide a composition for treating tumor growth comprising:

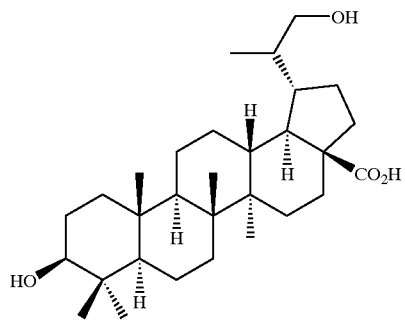

or

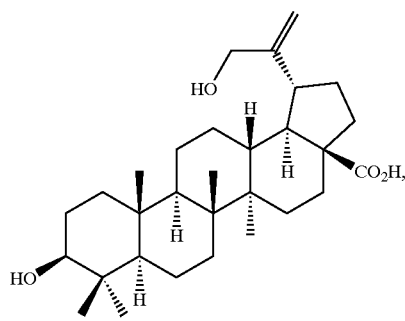

and (b) an optional carrier.

Another aspect of the present invention is to provide a composition for treating tumor growth comprising:

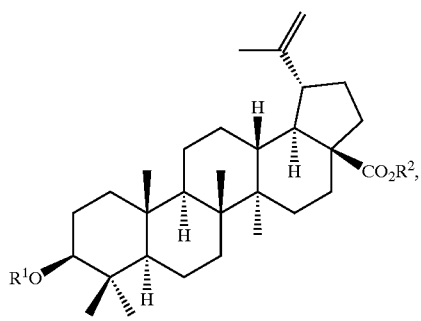

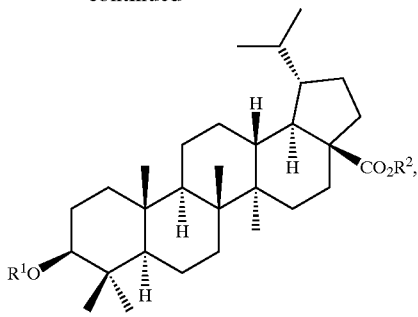

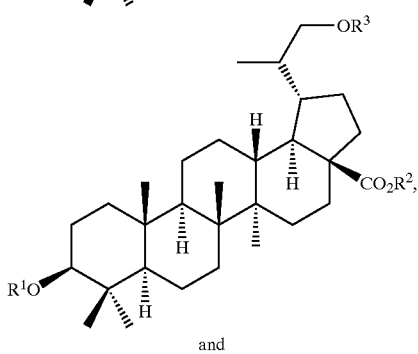

and

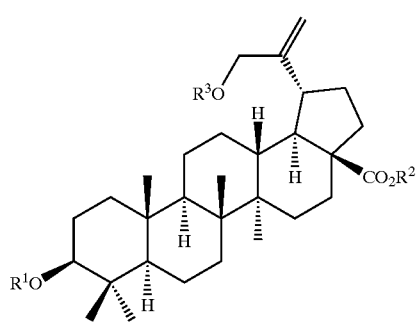

wherein $R^1$ and $R^3$, independently, are selected from the group consisting of hydrogen, $CO(C_1-C_6alkyl)NR^4R^5$, $CO(C_{1-3}alkyl)$ $CO_2R^4$, $COCH(C_6H_5)NR^4R^5$, $CO(C_1-C_6alkyl)$, $CO(C_1-C_6alkyl)$ $CO_2R^4$, $CO(C_{1-6}alkyl)O-(CH_2CH_2O)_nC_{1-3}alkyl$, $CH_2OCO_2C_{1-6}alkyl$, $CH_2OCOC_{1-6}alkyl$, $PO(OH)_2$, and $SO_3H$, $R^2$ is selected from the group consisting of hydrogen, $C_1-C_6alkyl$, $CH_2C_6H_5$, $C_1-C_6alkylNR^4R^5$, $CH_2OCOC_1-C_6alkyl$, $PO(OH)_2$, $SO_3H$, $CH(C_6H_5)NR^4R^5$, $(C_1-C_6alkyl)CO_2R^4$, and $(C_1-C_6alkyl)O(CH_2CH_2O)_nC_{1-3}alkyl$, $R^4$ and $R^5$, independently, are selected from the group consisting of hydrogen, $C_1-C_6alkyl$, $CO(C_1-C_6alkyl)$, and aryl, or $R^4$ and $R^5$ can be taken together to form a 5 to 7 membered ring, and n is 1 to 10;

and pharmaceutically acceptable salts thereof, and (b) an optional carrier.

Yet another aspect of the present invention is to provide a method of treating cancer sensitive to betulinic acid or a derivative thereof comprising administering to an individual in need thereof a therapeutically effective amount of a prodrug of betulinic acid or a derivative of betulinic acid. In particular, wherein the cancer is selected from the group consisting of a melanoma, a squamous tumor, a breast cancer, a colon cancer, a sarcoma, a human oral epidermal carcinoma, a hormone-dependent breast cancer, a prostate cancer, a lung cancer, a glioma, a melanoma, and a neuroblastoma.

These and other aspects of the present invention will become apparent from the following description of the invention, which are intended to limit neither the spirit nor scope of the invention but are only offered as illustrations of the preferred embodiments of the invention.

DETAILED DESCRIPTION OF THE PREFERRED EMBODIMENTS

Betulinic acid, 3β-hydroxy-lup-20 (29)ene-28-oic acid, is a natural, pentacyclic triterpene product isolated from several genus of higher plants. Betulinic acid has demonstrated remarkable selective antitumor activity against human melanoma (E. Pisha et al., *Nature Medicine*, 1, pp. 1046–1051 (1995)) and anti-HIV activity (T. Fujioka et al., *J. Nat. Prod.*, 57, pp. 243–247 (1994)).

Through a bioassay-directed fractionation of the stem bark of *Ziziphus mauritiana* Lam. (Rhamnaceae), betulinic acid was isolated as an active compound that showed a cytotoxicity against cultured human melanoma cells. Betulinic acid was found to be an excellent antitumor compound against human melanoma due to its unique in vitro and in vivo cytotoxicity profile. Betulinic acid showed a strong selective antitumor activity against melanoma by induction of apoptosis.

Betulinic acid also was found to have activity against the other cancer cell lines that were tested. The cytotoxicity of betulinic acid, and its lack of toxicity toward normal cells, afford a favorable therapeutic index. The cell lines evaluated for cytotoxicity were A431 (squamous), BC-1 (breast), ZR-75-1 (hormone-dependent human breast cancers), neuroblastoma, COL-2 (colon), HT-1080 (sarcoma), KB (human oral epidermoid carcinoma), LNCaP (prostate), LU-1 (lung), U373 (glioma), and MEL-1, -2, -3, and -4 (melanoma).

The bark of white birch, *Betula alba*, contains betulin (up to about 25%), lup-20 (29)-ene-3β,28-diol, and betulinic acid (0.025%), but it is difficult to isolate a sufficient quantity of betulinic acid to perform an extensive bioassay. It has been found that a quantity of betulinic acid could be provided from betulin through a simple synthetic approach.

As shown in Table 1, in vitro growth of MEL-2 cells was inhibited by betulinic acid, i.e., an $ED_{50}$ value of about 2 μg/ml. In this particular test, none of the other cancer cell lines tested was affected by betulinic acid (i.e., $ED_{50}$ values of greater than 20 μg/ml). The cytotoxic response mediated by betulinic acid is not exclusively limited to the MEL-2 melanoma cell line. Dose-response studies performed with additional human melanoma cell lines, designated MEL-1, MEL-3 and MEL-4, demonstrated $ED_{50}$ values of 1.1, 3.3 and 4.8 μg/ml, respectively.

As further illustrated in Table 1, other known antitumor agents, such as paclitaxel, camptothecin, ellipticine, homoharringtonine, mithramycin A, podopyllotoxin, vinblastine, and vincristine, demonstrated relatively intense, nonselective cytotoxic activity with no discernible cell-type selectivity.

In the following Table 1, the extracted betulinic acid and the other pure compounds were tested for cycotoxity against the following cultured human cell lines: A431 (squamous cells), BC-1 (breast), COL-2 (colon), HT-1080 (sarcoma), KB (human oral epidermoid carcinoma), LNCaP (prostate), LU-1 (lung), MEL-2 (melanoma), U373 (glioma) and ZR-75-1 (breast).

TABLE 1

Cytotoxic Activity Profile of the Crude Ethyl Acetate Extract Obtained from *Ziziphus mauritiana*, Betulinic acid, Other Antineoplastic Agents

| Compound | $ED_{50}$ (μg/ml) | | | | | | | | | |
| --- | --- | --- | --- | --- | --- | --- | --- | --- | --- | --- |
| | A431 | BC-1 | COL-2 | HT-1080 | KB | LNCaP | LU-1 | MEL-2 | U373 | ZR 75-1 |
| *Ziziphus mauritiana* crude extract | >20 | >20 | >20 | 9.5 | >20 | >20 | 5.2 | 3.7 | >20 | 15.8 |
| Betulinic acid | >20 | >20 | >20 | >20 | >20 | >20 | >20 | 2.0 | >20 | >20 |
| Taxol | 0.00 | 0.02 | 0.02 | 0.00 | 0.02 | 0.02 | 0.00 | 0.06 | 0.008 | 0.02 |
| Camptothecin | 0.00 | 0.07 | 0.005 | 0.01 | 0.00 | 0.006 | 0.00 | 0.02 | 0.000 | 0.001 |
| Ellipticine | 0.5 | 0.2 | 0.3 | 1.8 | 0.04 | 0.8 | 0.02 | 0.9 | 1.6 | 0.9 |
| Homoharringtonine | 0.02 | 0.03 | 0.1 | 0.01 | 0.00 | 0.03 | 0.03 | 0.04 | 0.2 | 0.06 |
| Mithramycin A | 0.09 | 0.3 | 0.06 | 1.5 | 0.09 | 0.05 | 0.2 | 1.2 | 0.04 | 0.2 |
| Podophyllotoxin | 0.03 | 0.03 | 0.005 | 0.00 | 0.08 | 0.04 | 0.00 | 0.003 | 0.004 | 0.4 |
| Vinblastine | 0.05 | 0.06 | 0.01 | 0.02 | 0.04 | 0.1 | 0.02 | 0.01 | 1.1 | 0.3 |
| Vincristine | 0.01 | 0.01 | 0.02 | 0.02 | 0.00 | 0.1 | 0.05 | 0.02 | 0.06 | 0.4 |

When using the test method used to develop the data in Table 1 (i.e., Method A), the greatest cytotoxic activity in response to betulinic acid was observed against human melanoma cells. Based on the data summarized in Table 1, in vivo studies using betulinic acid were performed. As set forth in Table 2, when betulinic acid was tested for cytotoxicity against cancer cell lines using other tests (i.e., Methods B and C), appreciable activity also was observed against other human cancer cell types (e.g., breast, sarcoma, lung, colon, squamous cell, prostate, and glioma). However, the greatest activity was observed against human melanoma cells. Betulinic acid also showed excellent cytotoxic activity against human neuroblastoma cell lines.

As confirmed by the data summarized in Table 1, betulinic acid has been reported as noncytotoxic with respect to cultured KB cells. Cytotoxicity of the crude extracts and purified compounds was determined in a number of cultured human cancer cell lines. Table 1 sets forth the various types of cancer cells evaluated using Method A. The cells were cultured in appropriate media and under standard conditions. To maintain logarithmic growth, the media were changed 24 hours prior to cytotoxic assays. On the day of the assay, the cells were harvested by trypsinization, counted, diluted in media, and added to 96-well plates containing test compounds dissolved in DMSO. The final DMSO concentration was 0.05%.

Table 2 summarizes test data showing the cytotoxicity of betulinic acid using test samples dissolved in tissue culture media (Method B) or 5% aqueous bovine serum albumin (Method C). Methods B and C illustrate the cytotoxicity of betulinic acid against cancer cell lines in addition to melanoma, particularly breast cancer, fibrosarcoma, lung cancer, colon cancer, epidermoid carcinoma, hormone-dependent breast cancer, and glioma.

In each of Methods A–C, the plates were incubated for three days. Following the incubation period, the cells were fixed and stained with sulforhodamine B (SRB) dye. The bound dye was liberated with Tris base, and the $OD_{515}$ (optical density at 515 nm) was measured on an ELISA reader. The growth of the betulinic acid-treated cells was determined by the $OD_{515}$ values, and the growth was compared to the $OD_{515}$ values of treated control cells of Methods A–C. Dose response studies were performed to generate ED50 values. As used herein, the term $OD_{515}$ is defined as optical density at 515 nM, and the term $ED_{50}$ is defined as the concentration of a compound required to reduce cell number by 50%.

was partitioned successively with hexane and ethyl acetate to provide hexane, ethyl acetate, and aqueous extracts. Among these extracts, the ethyl acetate (13.5 g) extract showed cytotoxic activity against a cultured melanoma cell line (MEL-2) with an $ED_{50}$ of 3.7 µg/ml. The ethyl acetate extract was chromatographed on a silica gel column using hexane-ethyl acetate (4:1 to 1:4) as eluent to give 10 fractions. Fractions 3 and 4 were combined and subjected to further fractionation to afford an active fraction (fraction 16) showing a major single spot by thin-layer chromatography ($R_f$ 0.67: $CHCl_3$:MeOH (chloroform:methanol) (10:1)), which yielded 72 mg of colorless needles after repeated crystallization from methanol (overall yield from dried plant material: 0.016% w/w).

The isolated active compound, betulinic acid ($ED_{50}$ of 2.0 µg/ml for MEL-2), has a molecular formula of $C_{30}H_{48}O_3$, as determined by high-resolution mass spectral analysis, a melting point range of 292–293° C. (decomposition). The literature melting point range for betulinic acid is 290–293°

TABLE 2

| Betulinic Acid | $ED_{50}$ (µg/ml) | | | | | | | | | | | |
|---|---|---|---|---|---|---|---|---|---|---|---|---|
| | BC1 | HT | Lu1 | Mel1 | Mel2 | Mel4 | Col2 | KB | A431 | LNCaP | ZA-75-1 | U373 |
| Method A | >20 | >20 | >20 | 1.1 | 1.9 | 4.8 | 17.2 | 19.2 | >20 | >20 | >20 | >20 |
| Method B | 11.2 | 11.3 | 7.7 | 0.9 | 0.9 | 1.6 | 13.3 | >20 | 12.1 | 19.3 | 6.4 | 12.1 |
| Method C | 12.6 | 10.0 | NT | NT | 1.6 | NT | NT | 16.6 | >20 | 16.6 | 6.9 | 18.7 |

Sample dissolved in 10% DMSO (Method A), tissue culture media (Method B), or 5% aqueous bovine serum albumin (Method C); BC1, human breast cancer; HT, human fibrosarcoma; Lu1, human lung cancer; Mel1, Mel2, Mel4, human melanoma; Col2, human colon cancer; KB, human oral epidermoid carcinoma; A431, human epidermoid carcinoma; LNCaP, human prostate cancer; ZA-75-1, hormone-dependent human breast cancer; U373, human glioma; NT, not tested.

The present invention, therefore, is directed to a method and composition for preventing or inhibiting tumor growth. The ultimate active compound is betulinic acid or a derivative of betulinic acid, which is generated in vivo from a prodrug of betulinic acid or derivative thereof. Betulinic acid can be isolated by a method comprising the steps of preparing an extract from the stem bark of *Ziziphus mauritiana* and isolating the betulinic acid. Alternatively, betulin can be isolated from the extract and used as a precursor for the synthesis of betulinic acid. The betulinic acid then is optionally converted to a betulinic acid derivative, followed by conversion of betulinic acid or derivative thereof to a prodrug.

Betulinic acid has the structural formula (1):

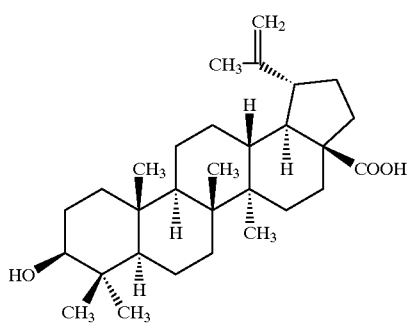

(1)

Betulinic acid is fairly widespread in the plant kingdom, and some biological activities have been reported.

Betulinic acid was obtained by extracting a sample of air-dried, milled stem bark (450 g) of *Z. mauritiana* with 80% aqueous methanol. The aqueous methanol extract then C. A mixed melting point range with a known sample of betulinic acid was not depressed. The optical rotation of the compound was measured as +7.3° (c=1.2; pyridine) (lit. +7.5°). The identity of the isolated compound as betulinic acid was confirmed by comparing the above physical properties, as well as $^1$H-NMR, $^{13}$C-NMR, and mass spectral data of the isolated compound, with physical data and spectra of a known sample of betulinic acid as reported in the literature.

Prodrugs of betulinic acid derivatives also can be used in the composition and method of the present invention. An examination of the structure of betulinic acid reveals that betulinic acid contains several positions, i.e., the C-3, C-20, C-28, C-29, and C-30 positions, where functional groups can be introduced. For example, see Pezzuto et al. U.S. Pat. No. 5,962,527, incorporated herein by reference. In addition, the introduced functional groups, if desired, then can be modified. Through a series of reactions at these five positions, a large number of betulinic acid derivatives were prepared and evaluated for bioefficacy against a series of human tumor cell lines, especially against human melanoma cell lines.

It is well established that a prodrug approach, wherein a drug is derivatized into a form suitable for formulation and/or administration, and then is released as the drug in vivo, has been successfully employed to transiently (e.g., bioreversibly) alter the physicochemical properties of the drug (see, H. Bundgaard, Ed., *Design of Prodrugs*, Elsevier, Amsterdam, (1985); R. B. Silverman, *The Organic Chemistry of Drug Design and Drug Action*, Academic Press, San Diego, chapter 8, (1992); K. M. Hillgren et al., *Med. Res. Rev.*, 15, 83 (1995)).

Generally, two strategies can be used to increase aqueous solubility of a drug compound: (a) introduction of an ionic or ionizable group and (b) derivatization in such a manner that the prodrug has a decreased melting point (see G. L.

Amidon, *Techniques of Solubilization of Drugs*, Yalkowsky et al., Ed., Marcel Dekker, New York, pp. 183–221, (1981)). Both the 3-OH and the carboxylic acid group (C-28) of betulinic acid are potential positions for such modifications. In addition, introduction of a hydroxy group at either the C-29 (2) or C-30 (3) position allows for similar modifications.

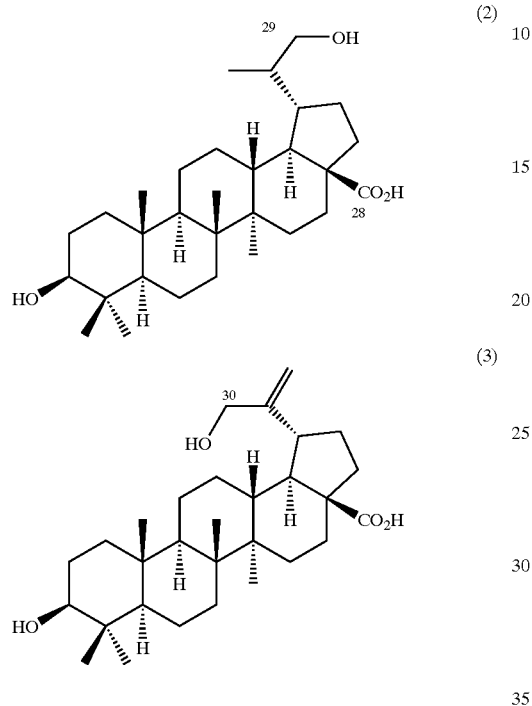

(2)

(3)

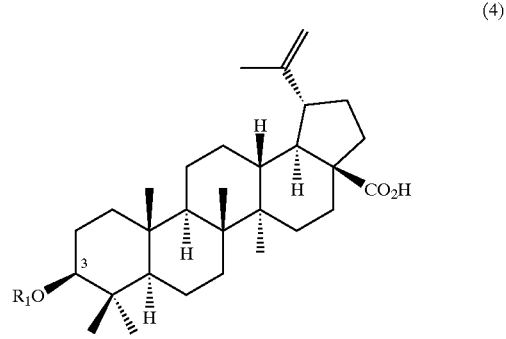

(4)

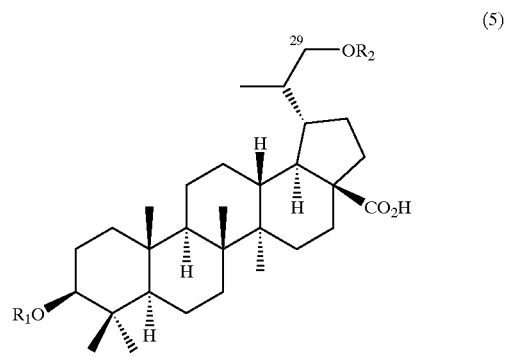

(5)

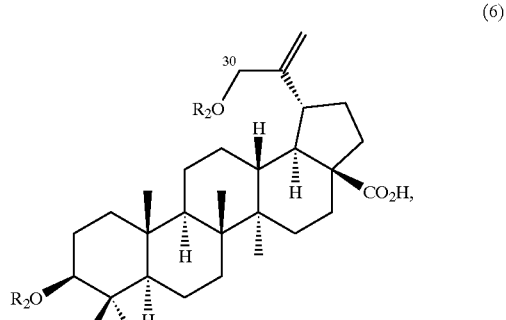

(6)

In the structures herein, for a bond lacking a substituent, the substituent is methyl, for example,

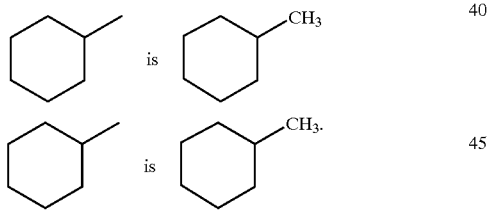

When no substituent is indicated as attached to a carbon atom on a ring, it is understood that the carbon atom contains the appropriate number of hydrogen atoms.

Among the ionic or ionizable promoieties, a hemisuccinate, a dialkylaminoacetate, and an amino acid ester are commonly used esters for increasing aqueous solubility of a hydroxy group-containing drug. Therefore, compounds 4a–4g, 5a–5g, and 6a–6g can be synthesized. Because the susceptibility of esters to undergo chemical and/or enzymatic hydrolysis varies widely, the present compounds, including both anionic and cationic moieties, are expected to be suitable substrates for a variety of endogenous hydrolytic enzymes, such as esterases, and to deliver the parent drug, i.e., betulinic acid or a betulinic acid derivative, bioreversibly.

wherein $R_1$ and $R_2$, independently, are selected from the group consisting of:

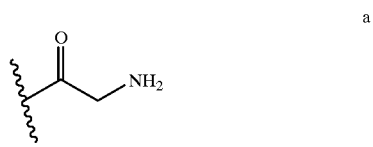

a

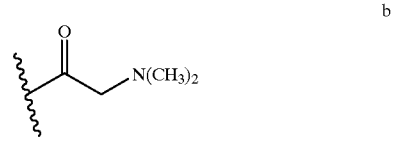

b

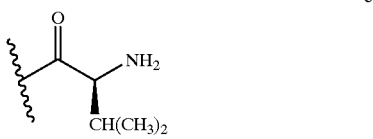

c

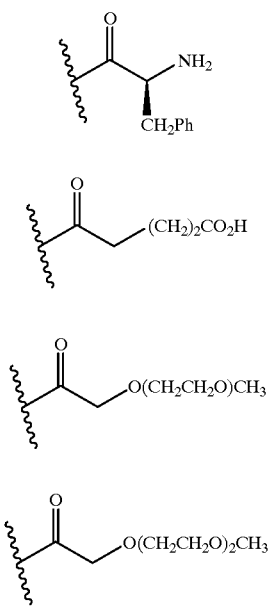

Phosphate prodrugs also can be used to overcome drug delivery problems that can compromise the therapeutic benefits of the parent drug (see, M. G. Nicolaou et al., *J. Org. Chem.*, 61, 8636, (1996), for example). In the presence of alkaline phosphatase, an enzyme widely distributed in a variety of tissues such as the liver, kidney tubules, and intestinal epithelium, for example, phosphomonoesters can undergo hydrolysis to release the parent hydroxy-containing drug and an inorganic phosphate. The phosphate prodrugs 7–9 are designed to be a substrate for the endogenous alkaline phosphatases.

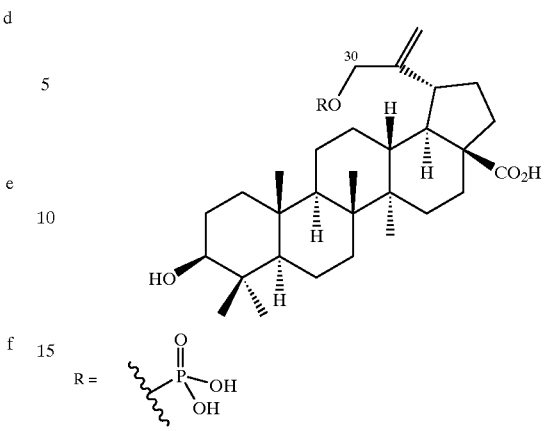

Compounds 10a–10b, 11a–11g, and 12a–12g are pivaloyloxymethyl derivatives. This (acyloxy)alkyl class of prodrugs have proven useful with respect to improving the biological availability of a parent carboxylic acid, as well as alcohols (see, N. Bodor et al., *Int. J. Pharm.*, 7, 63 (1980); and N. Bodor et al., *J. Org. Chem.*, 48, 5280 (1983)). For example, the 3-pivalyloxymethyl ether of 17β-estradiol substantially reduced the melting point of the parent 17β-estradiol. It is theorized, but not relied upon herein, that a pivalyloxymethyl prodrug, after absorption, is hydrolyzed enzymatically by nonspecific esterases to the corresponding hydroxy-methyl derivative, which subsequently decomposes spontaneously to betulinic acid (or betulinic acid derivative) and formaldehyde.

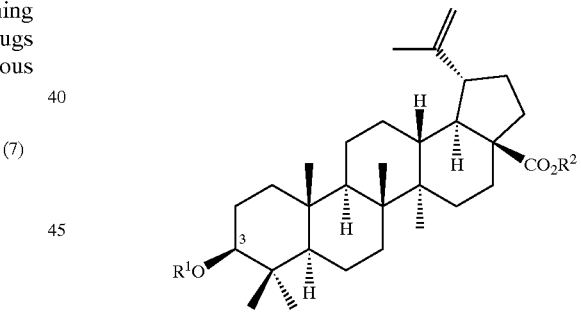

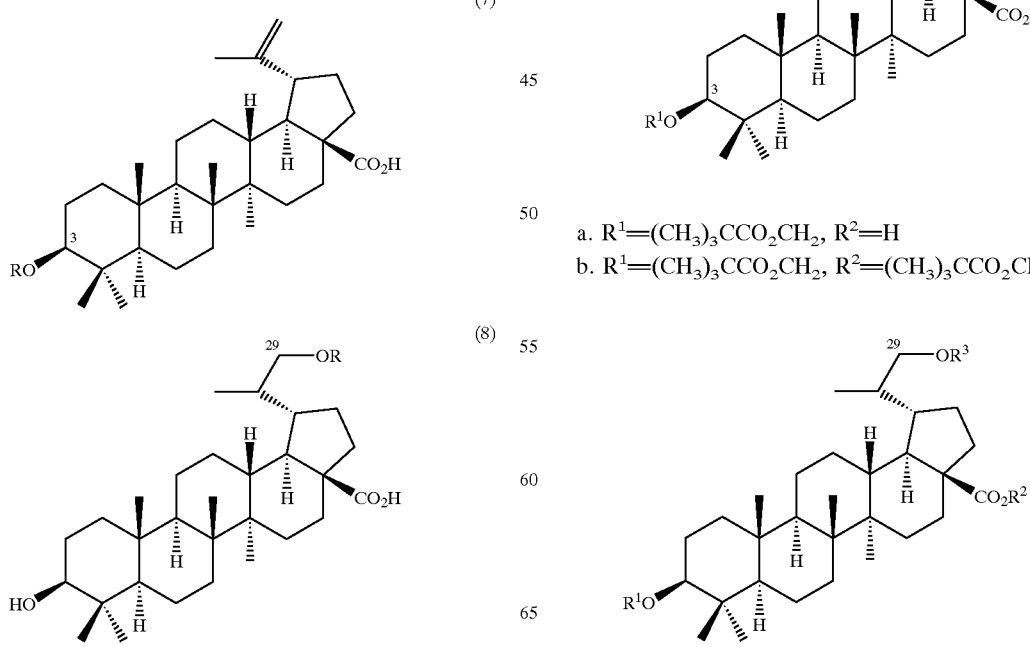

a. $R^1=(CH_3)_3CCO_2CH_2$, $R^2=H$
b. $R^1=(CH_3)_3CCO_2CH_2$, $R^2=(CH_3)_3CCO_2CH_2$ (12)

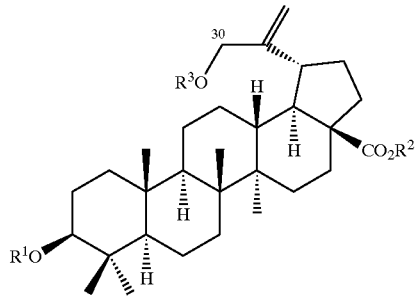

a. R¹=(CH₃)₃CCO₂CH₂, R²=H, R³=H
b. R¹=H, R²=(CH₃)₃CCO₂CH₂, R³=H
c. R¹=H, R²=H, R³=(CH₃)₃CCO₂CH₂
d. R¹=(CH₃)₃CCO₂CH₂, R²=(CH₃)₃CCO₂CH₂, R³=H
e. R¹=(CH₃)₃CCO₂CH₂, R²=H, R³=(CH₃)₃CCO₂CH₂
f. R¹=H, R²=(CH₃)₃CCO₂CH₂, R³=(CH₃)₃CCO₂CH₂
g. R¹=(CH₃)₃CCO₂CH₂, R²=(CH₃)₃CCO₂CH₂, R³=(CH₃)₃CCO₂CH₂

Another class of prodrugs of the present invention is sulfates of betulinic acid (13) and betulinic acid derivatives (14a–c, 15a–c). The sulfate moiety increases the hydrophilicity of the compounds, while endogenous nonspecific sulfatases release betulinic acid or a betulinic acid derivative and an inorganic sulfate in vivo.

(13)

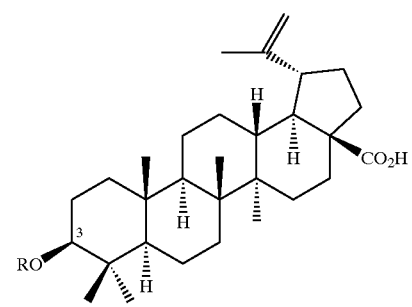

R = SO₃H (14)

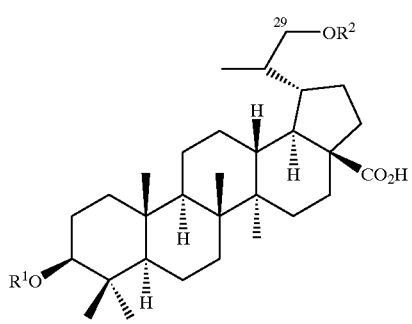

(15)

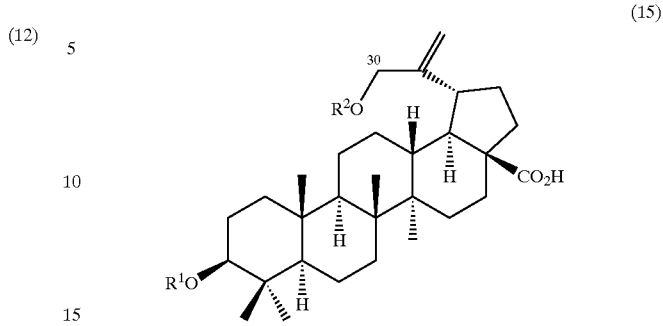

a. R¹=SO₃H, R²=H
b. R¹=H, R²=SO₃H
c. R¹=SO₃H, R²=SO₃H

Synthesis of Betulinic Acid

Even though betulinic acid has been isolated from several genus of higher plants, the abundance of betulinic acid is sufficiently low such that it is tedious to isolate in a useable quantity (see, T. Fujioka et al., *J. Nat. Prod.*, 57, 243-7 (1994); S. Siddiqui et al., *J. Nat. Prod.*, 57, 243-7 (1994); and F. Robinson et al., *Phytochemistry*, 9, 907-9 (1970)). However, as noted previously, betulin 16, is readily available from the bark of white birch, in concentrations up to about 25% by weight, and hundreds of tons of the bark are discarded each year in processes such as furniture manufacture.

Two synthetic methods for the production of betulinic acid from betulin have been reported. One method involves three steps with an overall 71% yield, and the second method is a five-step process affording an overall 55% yield (see D. S. H. L. Kim et al., *Synth. Commun.*, 27, 1607–1612 (1997). The first method produced a higher overall yield in the laboratory, but the product is difficult to purify during scale up because the undesirable 3α-isomer was formed as a by-product. The second method, although providing a lower yield, does not produce the undesired 3α-isomer, and involves predominantly protecting and deprotecting procedures, and thus is preferred for the synthesis of betulinic acid.

Therefore, betulin 16 can be isolated from the bark of *Betula alba*, following a literature method, and converted to betulinic acid as shown in following Scheme 1. Briefly, the primary hydroxy group of betulin is selectively protected as a tetrahydropyran (THP) ether 17 in step i), then the secondary hydroxy group is acetylated to provide compound 18 in step ii). After the THP group in compound 18 is selectively removed in step iii), the resulting primary alcohol 19 is oxidized under Jones oxidation conditions (CrO₃/H₂SO₄/acetone/0° C.) in step iv) to provide carboxylic acid 20. The acetyl group finally is removed under mild basic conditions in step v) to yield betulinic acid.

Scheme 1

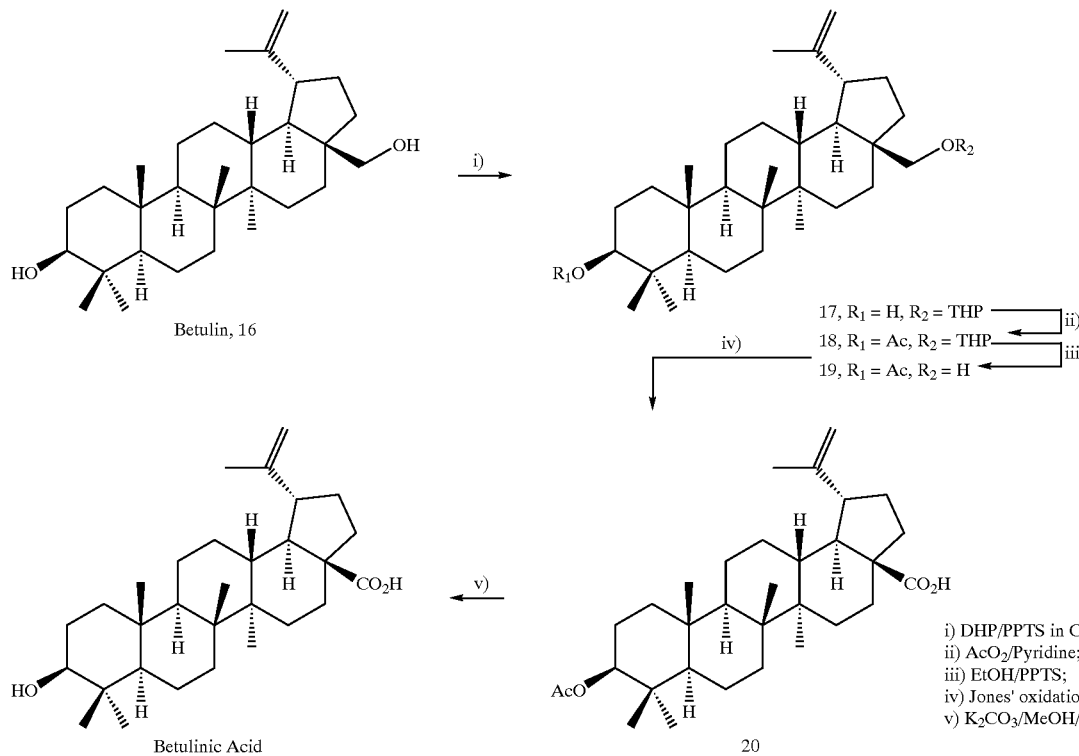

Synthesis of C-29 and C-30 Betulinic Acid Alcohols

The synthesis of betulinic acid derivatives 2 and 3 is accomplished by hydroboration and allylic oxidation, respectively. The C-29 alcohol is synthesized from the common intermediate 20, with additional protection of the carboxylic acid as the benzyl ester (21). Hydroboration of (21) with $BH_3$-dimethyl sulfide, followed by oxidation under basic conditions yields the C-29 alcohol (22), which then is selectively functionalized without interference of the C-3 alcohol or C-28 carboxylic acid. Hydrolysis of the C-3 acetate followed by catalytic hydrogenolysis of the C-28 benzyl ester yields the unprotected C-29 alcohol.

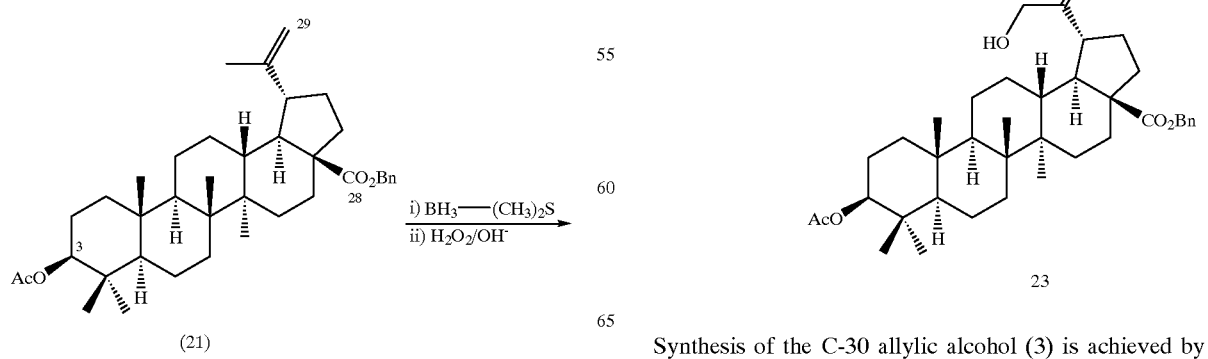

Synthesis of the C-30 allylic alcohol (3) is achieved by reaction of the protected betulinic acid (21), followed by oxidation with catalytic selenium dioxide and t-butyl hydroperoxide. The protected C-30 allylic alcohol (23) can be further manipulated as desired, and the C-3 acetate and C-28 benzyl ester can be removed by hydrolysis with potassium carbonate.

To synthesize prodrugs 2a–g, the carboxylic acid group in betulinic acid is protected. A variety of protecting groups can be employed. Because the ester group in the present prodrugs may be labile, a protecting group capable of being removed under very mild conditions is used. One preferred protecting agent is a benzyl group because a benzyl group is readily cleaved by hydrogenolysis under neutral conditions. The 20(29)-ene double bond in betulinic acid can be saturated during hydrogenolysis. However, the benzyl group can be cleaved in the presence of a double bond by using t-BuMe$_2$SiH and Pd(OAc)$_2$ (see, M. Sakaitgani et al., Tetrahedron Lett., 27, 3753 (1986)). Therefore, the benzyl ester of betulinic acid 26 is prepared from the acetate 20. Reaction of acetate 20 with benzyl bromide in the presence of potassium carbonate (K$_2$CO$_3$) in acetone yields the double ester 21, which is deacetylated using K$_2$CO$_3$ in methanol (MeOH) as described above, providing precursor 26 (Scheme 2).

Alternatively, a direct, one-step benzylation of betulinic acid using benzyl bromide in the presence of K$_2$CO$_3$ in acetone yielded precursor 26 in an acceptable yield (Scheme 2).

activated with CDI at room temperature for 2 hours, then refluxed with betulinic acid overnight to provide (4i) in 97% yield. Boc is an abbreviation for t-butylcarboxy. Deprotection of the Boc group with trifluoroacetic acid/dichloromethane (TFA/DCM) resulted in rearrangement of the betulinic acid ring system. After trying several methods, it was found that 4M HCl in dioxane cleaves the Boc group without attacking the betulinic acid ring system.

By a similar method, products (4f) and (4j) were synthesized according to synthetic scheme 3.

The hemisuccinate derivative (4g) was prepared according to a literature method (L. Colla et al., J. Med. Chem., 26, 602 (1983)) by reacting benzyl ester 26 with succinic anhydride in the presence of triethylamine in DMF, followed by debenzylation (Scheme 4). This scheme also is used to prepare derivatives (5g) and (6g).

Scheme 3

Synthesis of Betulinic Acid Ester Prodrugs

Compounds (4), (5), and (6a–d) are amino acid esters synthesized according to the conventional methods. Thus, when activated by carbonyldiimidazole (CDI) or dicyclohexylcarbodiimide (DCC) in refluxing tetrahydrofuran (THF), benzyl ester 26 reacts with N,N-dimethylglycine, or Cbz-protected amino acids, such as glycine, L-leucine and L-phenylalanine, respectively (Scheme 3). Cbz is an abbreviation for carboxybenzoyl. The formed esters 27a–d are treated with t-butyldimethylsilane (t-BuMe$_2$SiH) in the presence of Pd(OAc)$_2$ to cleave the benzyl as well as Cbz-protecting groups, resulting in the formation of compounds (4a–d). The same scheme can be used to synthesize compounds (4e), (4f), (5a–f), and (6a–f) via (27a–f), respectively. All the carboxylic acids employed are commercially available.

Alternatively, free acid analogues (4) can be synthesized directly from betulinic acid (Scheme 3). Boc-Gly-OH was

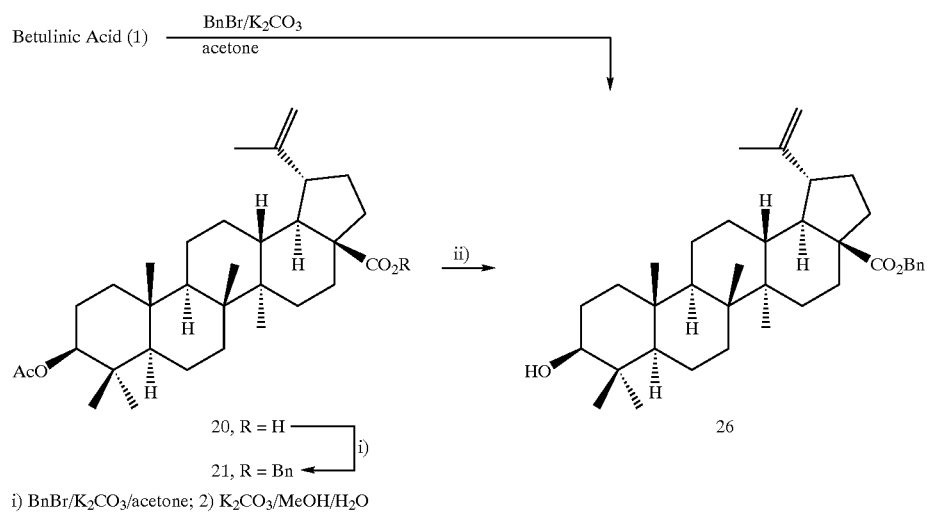

i) BnBr/K$_2$CO$_3$/acetone; 2) K$_2$CO$_3$/MeOH/H$_2$O

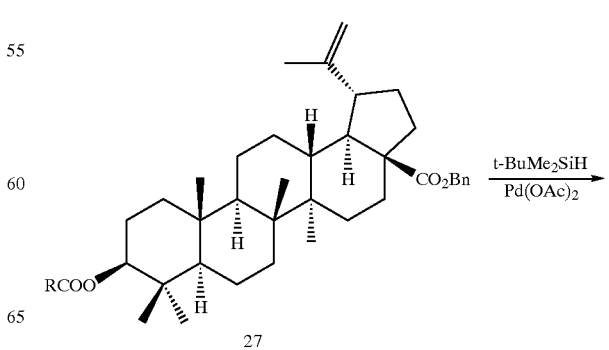

-continued

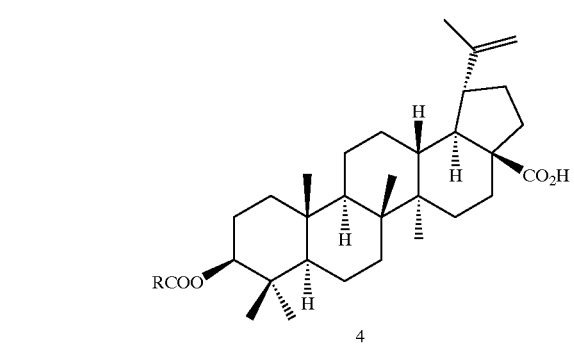

Betulinic Acid (1) $\xrightarrow{\text{RCOOH}}{\text{CDI, THF}}$

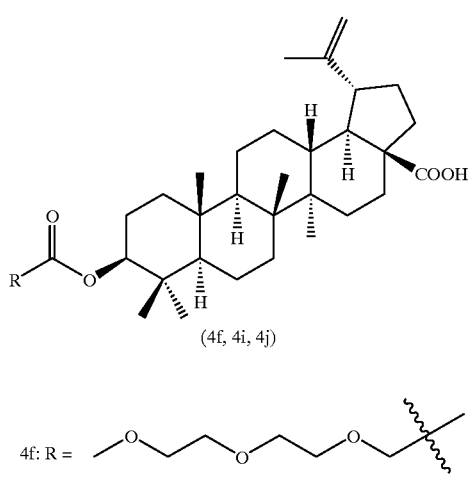

(4f, 4i, 4j)

4f: R = 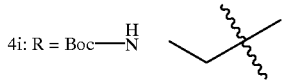

4i: R = Boc—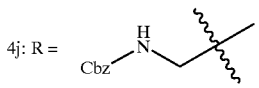

| R in 27 | R in 4 |
|---|---|
| CH$_2$NHCbz (27a) | CH$_2$NH$_2$ (4a) |
| CH$_2$NMe$_2$ (27b) | CH$_2$NMe$_2$ (4b) |
| 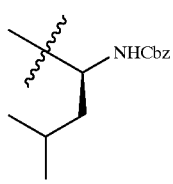 | 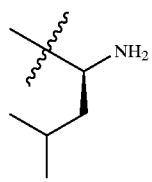 |
| (27c) | (4c) |

| R in 27 | R in 4 |
|---|---|
| 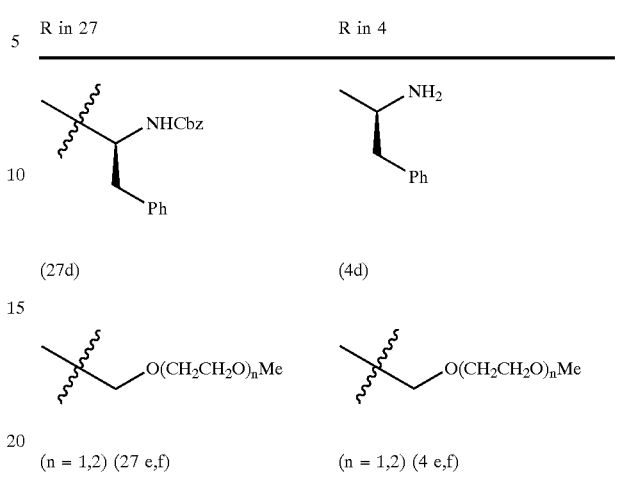 | |
| (27d) | (4d) |
| (n = 1,2) (27 e,f) | (n = 1,2) (4 e,f) |

Cbz = carboxybenzoyl
Me = methyl
Ph = phenyl

Scheme 4

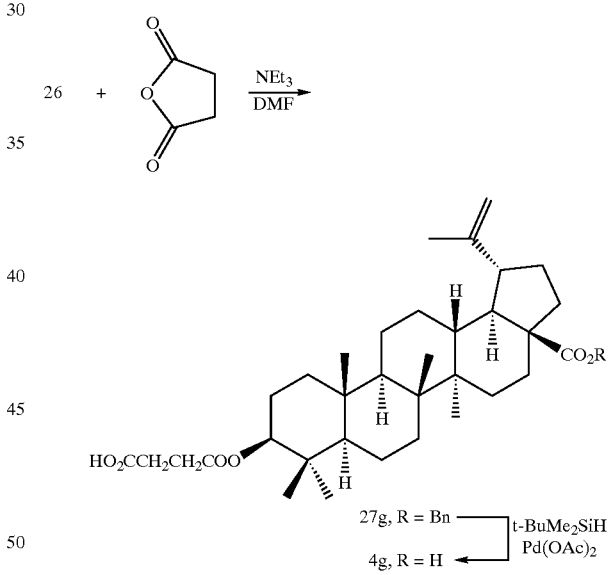

27g, R = Bn ⎤ t-BuMe$_2$SiH
4g, R = H ⎦ Pd(OAc)$_2$

Synthesis of Phosphate Prodrugs (7–9)

The commercially available tetrabenzyl-pyrophosphate (TBPP) is a suitable phosphorylating agent. Thus, treatment of benzyl ester 26 with butyllithium in THF, followed by TBPP, can afford phosphate diester (7) after aqueous workup (Scheme 5). Debenzylation is achieved by treatment with t-BuMe$_2$SiH in the presence of Pd(OAc)$_{21}$ providing phosphoric carboxylic acid (7). This route is also used for derivatives (8) and (9).

4j: R = 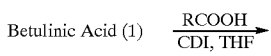

Scheme 5

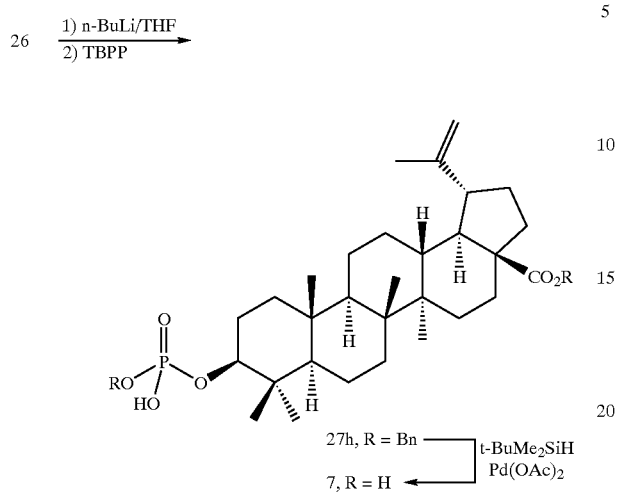

Synthesis of Acyloxyalkyl Derivatized Prodrugs (10–12)

Chloromethyl pivalate is commercially available, and other chloromethyl esters can be prepared by published literature methods (see, Eurato et al., *Acta Chem. Scand.*, 20, 1276 (1966)). Reaction of the sodium or lithium salt of benzyl ester 26 with chloromethyl pivalate provides pivaloyloxy-methyl derivative 27i (Scheme 6). Debenzylation of 27i with t-BuMe$_2$SiH and Pd(OAc)$_2$ produces the corresponding monopivaloyloxymethyl compound 10a. Treatment of the disodium salt of betulinic acid with chloromethyl pivalate furnishes the bis-pivaloyloxy-methyl compound 10b (Scheme 6). The literature reports that chloromethyl esters may not be sufficiently reactive, and, accordingly, can be converted to the corresponding iodo analogues by treatment with NaI.

Scheme 6

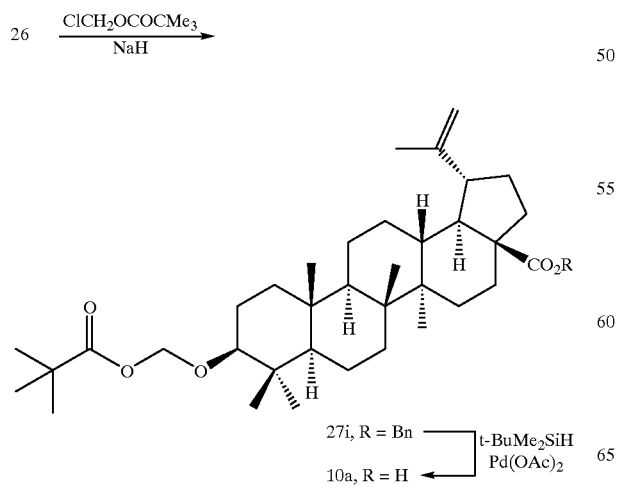

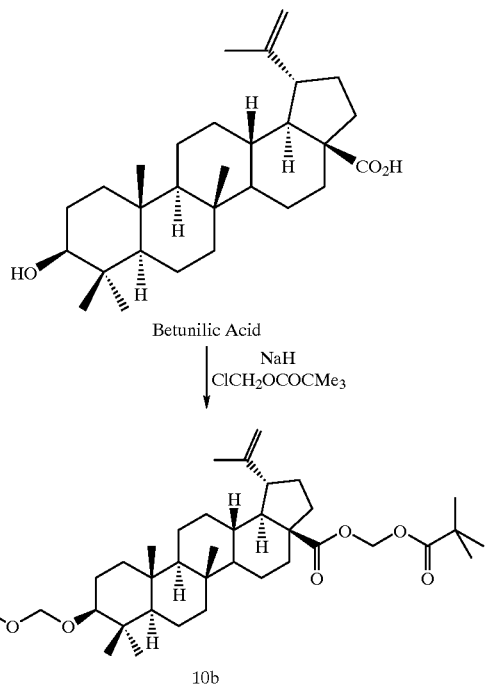

Hydrogenolysis of benzylesters (27a)–(27i) yielded the corresponding 20(29)-saturated betulinic acid (28a)–(27i) (Scheme 7).

Scheme 7

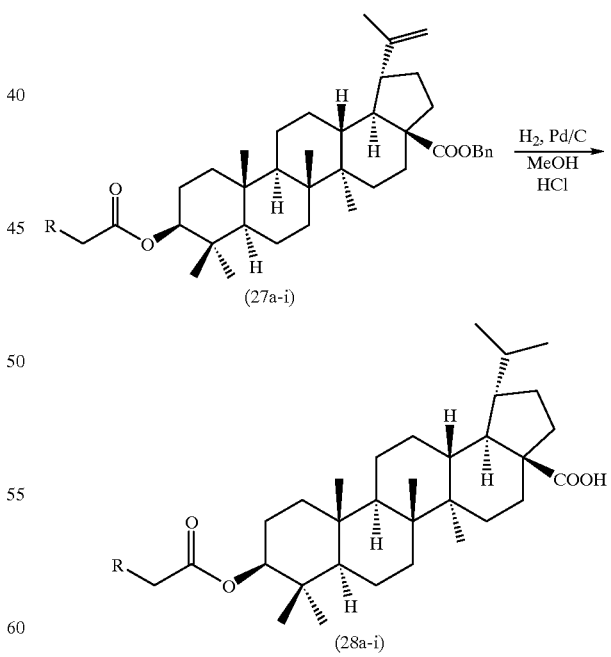

The following abbreviations are used in the synthetic procedures: K$_2$CO$_3$ (potassium carbonate), MgSO$_4$ (magnesium sulfate), EtOAc (ethyl acetate), THF (tetrahydrofuran), NaH (sodium hydride), HCl (hydrochloric acid), and Et$_2$O (diethyl ether)

Synthesis of Benzyl-Protected Betulinic Acid (26)

Betulinic acid (9.76 g, 21.41 mmole) and K$_2$CO$_3$ (4.37 g, 31.62 mmole) in acetone (500 ml) was stirred for 20 minutes. Then, benzyl bromide (6.4 ml, 53.81 mmole) was added, and the resulting mixture was stirred at room temperature overnight. Additional benzyl bromide (4.0 ml, 33.63 mmole) was added, and the mixture was stirred for an additional 24 hours at room temperature. The solvent was evaporated, water was added to the residue, then extracted with ethyl acetate. The EtOAc extracts were washed with brine, and dried over anhydrous MgSO$_4$. After removal of solvent, the crude product was purified by silica column using 10% EtOAc/hexane as an eluent to give 7.55 g (64% yield) of product as white solid. $^1$H NMR (CDCl$_3$) δ 0.6–1.7 (m, 38H), 1.8–1.9 (m, 2H), 2.1–2.35 (m, 2H), 2.95–3.05 (m, 1H), 3.1–3.2 (m, 1H), 4.59 (d, J=2 Hz, 1H), 4.72 (d, J=2 Hz,1H), 5.12 (m, 2H), 7.3–7.4 (m, 5H). MS (APCI$^+$): 547.2 (M+1), 529.2 (M-H$_2$O). FT-IR (cm$^{-1}$): 3553, 2940, 2866, 1692, 1451.

Synthesis of Cbz-Gly Ester Derivative (27a)

To a solution of Cbz-Gly-OH (209 mg, 1 mmol) in THF (10 ml) was added CDI (162 mg, 1 mmol). The mixture was stirred at room temperature for 30 minutes, then betulinic acid benzyl ester (26) (238 mg, 0.44 mmol) was added. The resulting mixture was refluxed for one day. The reaction mixture then was diluted with water and extracted three times with EtOAc. The organic layer was washed with brine, and dried over MgSO$_4$. After removal of solvent, the residue was purified by a column chromatography on silica gel with EtOAc/hexane as an eluent to give 130 mg of Cbz-Gly-betulinic acid ester derivative (27a). Yield: 41%. m.p.: 55–57° C. $^1$H NMR (CDCl$_3$) δ: 0.6–1.7 (m, 38H), 1.8–2.0 (m, 2H), 2.1–2.35 (m, 2H), 2.95–3.1 (m, 1H), 3.95 (d, J=5.4 Hz, 2H), 4.55 (m, 1H), 4.59 (s, 1H), 4.72 (s, 1H), 5.12 (m, 4H), 5.3 (br, 1H), 7.3–7.4 (m, 10H). MS (ESI$^+$): 755.6 (M+NH$_4$). FT-IR (cm$^{-1}$) 3425, 2943, 2869, 1722, 1453. Anal. Calcd for C$_{47}$H$_{63}$N$_1$O$_6$: C, 76.49; H, 8.60; N, 1.90; Found: C, 75.38; H, 8.76; N, 1.83.

Synthesis of Cbz-Phe Ester Derivative (27d)

Compound (27d) was synthesized by reacting Cbz-Phe-OH with the betulinic acid benzyl ester (26) by a similar method as described to prepare compound (27a). Yield: 15%. m.p. 67–71° C. $^1$H NMR (CDCl$_3$) δ: 0.70–1.71 (m, 38 H), 1.80–1.95 (m, 2H), 2.1–2.3 (m, 2H), 2.95–3.15 (m, 3H), 4.4–4.5 (m, 1H), 4.6–4.65 (m, 1H), 4.59 (d, J=2 Hz, 1H), 4.72 (d, J=2 Hz, 1H), 5.12 (m, 4H), 5.22 (d, J=8 Hz, 1H), 7.1–7.4 (m, 15H). MS (ESI$^+$): 845.6 (M+NH$_4$), 828.5 (M+1). FT-IR (cm$^{-1}$): 3431, 2944, 2868, 1722, 1497. Anal. Calcd for C$_{54}$H$_{69}$N$_1$O$_6$: C, 78.32; H, 8.40; N, 1.69; Found: C, 78.01; H, 8.52; N, 1.61.

Synthesis of Cbz-Leu Ester Derivative (27c)

Compound 27c was synthesized by reacting Cbz-Leu-OH with the betulinic acid benzyl ester (26) by a similar method as described to prepare compound (27a). Yield: 6%. m.p. 64–69° C. $^1$H NMR (CDCl$_3$) δ: 0.7–1.8 (m, 47H), 1.8–2.0 (m, 2H), 2.1–2.3 (m, 2H), 2.95–3.1 (m, 1H), 4.3–4.4 (m, 1H), 4.45–4.55 (m, 1H), 4.59 (d, J=2 Hz, 1H), 4.72 (d, J=2 Hz, 1H), 5.08–5.20 (m, 4H), 7.3–7.4 (m, 10H). MS (APCI$^+$): 812.4 (M+NH$_4$), 794.7 (M+1). FT-IR (cm$^{-1}$): 3355, 2946, 2868, 1722, 1453. Anal. Calcd for C$_{51}$H$_{71}$N$_1$O$_6$: C, 77.14; H, 9.01; N, 1.76; Found: C, 77.36; H, 9.11; N, 1.69.

Synthesis of 2-(2-Methoxyethoxy)acetic Acid Ester Derivative (27e)

Compound (27e) was synthesized by reacting 2-(2-methoxyethoxy)acetic acid with the betulinic acid benzyl ester (26) by a similar method as described to prepare compound (27a). Yield: 38%. $^1$H NMR (CDCl$_3$) δ: 0.75–1.7 (m, 38H), 1.85–1.95 (m 2H), 2.1–2.3 (m, 2H), 2.95–3.10 (m, 1H), 3.38 (s, 3H), 3.58 (m, 2H), 3.72 (m, 2H), 4.13 (s, 2H), 4.5–4.6 (m, 1H), 4.59 (s, 1H), 4.72 (s, 1H), 5.12 (m, 2H), 7.3–7.4 (m, 5H). MS (ESI$^+$): 680.6 (M+NH$_4$). FT-IR (cm$^{-1}$): 2945, 2867, 1754, 1715, 1453. Anal. Calcd for C$_{42}$H$_{62}$O$_6$: C, 76.09; H, 9.43; Found: C, 76.28; H, 9.47.

Synthesis of 2-[2-(2-Methoxyethoxy)ethoxy]acetic Acid Ester Derivative (27f)

Compound (27f) was synthesized by reacting 2-[2-(2-methoxyethoxy)ethoxy]acetic acid with the betulinic acid benzyl ester (26) by a similar method as described to prepare compound (27a). Yield: 52%. $^1$H NMR (CDCl$_3$) δ: 0.75–1.7 (m, 38H), 1.85–1.95 (m 2H), 2.05–2.3 (m, 2H), 2.95–3.10 (m, 1H), 3.38 (s, 3H), 3.57 (m, 2H), 3.6–3.75 (m, 6H), 4.13 (s, 2H), 4.5–4.6 (m, 1H), 4.59 (d, J=2 Hz, 1H), 4.72 (d, J=2 Hz, 1H), 5.12 (m, 2H), 7.3–7.4 (m, 5H). MS (APCI$^+$): 724.3 (M+NH$_4$). FT-IR (cm$^{-1}$): 2942, 2869, 1724, 1454. Anal. Calcd for C$_{44}$H$_{66}$O$_6$: C, 74.75; H, 9.41; Found: C, 73.72; H, 9.34.

Synthesis of Pivaloyoxymethyl Ether Derivative (27i)

To a solution of betulinic acid benzyl ester (26) (526 mg, 0.96 mmol) in THF (10 ml) was added NaH (60%, 66 mg, 1.6 mmol). The mixture was stirred at room temperature for 1 hour, then chloromethyl pivalate (635 mg, 0.96 mmol) was added. The resulting mixture was stirred at room temperature overnight. The reaction mixture then was diluted with water, and extracted three times with ethyl acetate. The organic layer was washed with brine, and dried over MgSO$_4$. After removal of solvent, the residue was purified by column chromatography on silica gel with EtOAc/hexane as an eluent to give 102 mg of the desired product (27i). Yield: 16%. m.p.: 122–128° C. $^1$H NMR (CDCl$_3$) δ: 0.7–1.7 (m, 47H), 1.85–1.95 (m, 2H), 2.1–2.3 (m, 2H), 2.95–3.15 (m, 2H), 4.59 (d, J=2 Hz, 1H), 4.72 (d, J=2 Hz, 1H), 5.12 (m, 2H), 5.27 (d, J=6 Hz, 1H), 5.35 (d, J=6 Hz, 1H), 7.3–7.4 (m, 5H). MS (ESI$^+$): 678.7 (M+NH$_4$). FT-IR (cm$^{-1}$): 2947, 2866, 1746, 1714, 1480. Anal. Calcd for C$_{43}$H$_{64}$O$_5$: C, 78.14; H, 9.76; Found: C, 78.46; H, 10.49.

Synthesis of Boc-Gly Ester Derivative (4i)

To a solution of Boc-Gly-OH (525 mg, 3 mmol) in THF (5 ml) was added CDI (486 mg, 3 mmol). The mixture was stirred at room temperature for 2 hours, then betulinic acid (684 mg, 1.5 mmol) was added. The resulting mixture was refluxed overnight. After removal of solvent, the residue was dissolved in dichloromethane, washed with water, followed by brine, and dried over Na$_2$SO$_4$. After removal of solvent, the residue was purified by a column chromatography on silica gel with EtOAc/-hexane as an eluent to give 900 mg of Boc-Gly-betulinic acid derivative (4i). Yield: 97%. m.p.: 135–136° C. $^1$H NMR (DMSO-d$_6$) δ: 0.75–1.7 (m, 47H), 1.75–1.9 (m, 2H), 2.05–2.3 (m, 2H), 2.9–3.0 (m, 1H), 3.63 (d, J=6 Hz, 2H), 4.4 (m, 1H), 4.56 (d, J=2 Hz, 1H), 4.69 (d, J=2 Hz, 1H), 7.18 (t, J=6 Hz, 1H), 12.05 (s, 1H). MS (ESI$^-$): 612.4 (M-1). FT-IR (cm$^{-1}$): 2943, 2869, 1702. Anal. Calcd for C$_{37}$H$_{59}$N$_1$O$_6$: C, 72.39; H, 9.69; N, 2.28; Found: C, 72.13; H, 10.07; N, 2.20.

Synthesis of Cbz-Gly Ester Derivative (4j)

Compound (4j) was synthesized by reacting Cbz-Gly-OH with the betulinic acid by a similar method as described to prepare compound (IIIb). Yield: 7%. m.p.: 82–88° C. $^1$H NMR (CDCl$_3$) δ: 0.75–1.7 (m, 38H), 1.95–2.05 (m, 2H), 2.1–2.3 (m, 2H), 2.95–3.05 (m, 1H), 3.97 (d, J=6 Hz, 2H), 4.5–4.6 (m, 1H), 4.60 (s, 1H), 4.75 (s, 1H), 5.12 (s, 2H), 5.25 (m, 1H), 7.3–7.4 (m, 5H). MS (APCI$^-$): 646.9 (M+NH$_4$). FT-IR (cm$^{-1}$): 2943, 2869, 1708. Anal. Calcd for C$_{40}$H$_{57}$N$_1$O$_6$: C, 74.15; H, 8.87; N, 2.16; Found: C, 71.57; H, 8.67; N, 2.22.

Synthesis of 2-[2-(2-Methoxyethoxy)ethoxy]acetic Acid Ester Derivative (4f)

Compound (4f) was synthesized by reacting 2-[2-(2-methoxyethoxy)ethoxy]acetic acid with the betulinic acid by a similar method as described to prepare compound (IIIb).

Yield: 52%. $^1$H NMR (CDCl$_3$) δ: 0.8–1.7 (m, 38H), 1.9–2.0 (m 2H), 2.1–2.3 (m, 2H), 2.95–3.05 (m, 1H), 3.38 (s, 3H), 3.57 (m, 2H), 3.6–3.75 (m, 6H), 4.13 (s, 2H), 4.5–4.6 (m, 1H), 4.61 (d, J=2 Hz, 1H), 4.74 (d, J=2 Hz, 1H). MS (APCI–): 615.8 (M–1). FT-IR (cm$^{-1}$): 2937, 2869, 1729, 1694. Anal. Calcd for C$_{37}$H$_{60}$O$_6$: C, 72.04; H, 9.80; Found: C, 71.98; H, 9.90.

Synthesis of Gly Ester Derivative (4a)

Compound (4a) (61 mg, 0.1 mmol) was dissolved in 4M HCl dioxane solution and stirred at room temperature for 10 min. The reaction mixture was diluted with toluene (3 ml). After removal of solvent under vacuum, the residue was washed with Et$_2$O to afford 25 mg of the desired product as a white solid. Yield: 45%. m.p.: 275° C. (dec). $^1$H NMR (DMSO-d$_6$) δ: 0.8–1.7 (m, 38H), 1.75–1.9 (m 2H), 2.1–2.3 (m, 2H), 2.9–3.0 (m, 1H), 3.8–3.9 (m, 2H), 4.5–4.6 (m, 1H), 4.56 (s, 1H), 4.69 (s, 1H), 8.30 (br, 3H). MS (APCI$^-$): 514.6 (M+1). FT-IR (cm$^{-1}$): 2941, 2869, 1740. Anal. Calcd for C$_{32}$H$_{52}$ClNO$_4$: C, 69.85; H, 9.53; N, 2.55; Found: C, 66.31; H, 9.38; N, 2.68.

Synthesis of Gly Ester Saturated Derivative (28a)

Compound (27a) (180 mg, 0.28 mmol) was dissolved in EtOAc (5 ml), diluted with methanol (10 ml), and one drop of HCl solution (6N) was added. The reaction mixture was hydrogenated with 50 mg of 10% palladium on activated carbon as a catalyst at 50 psi hydrogen pressure at room temperature for 4 hrs. The catalyst was removed by filtration. After removal of solvent, the residue was washed with Et$_2$O to afford 110 mg of the desired product as a white solid. Yield: 72%. m.p.: 285° C. (dec). $^1$H NMR (DMSO-d$_6$) δ: 0.8–1.7 (m, 38H), 1.75–1.9 (m 2H), 2.1–2.3 (m, 2H), 2.9–3.0 (m, 1H), 3.8–3.9 (m, 2H), 4.5–4.6 (m, 1H), 4.56 (s, 1H), 4.69 (s, 1H), 8.30 (br, 3H). MS (ESI$^+$): 516.1 (M+1). FT-IR (cm$^{-1}$): 2947, 2868, 1740. Anal. Calcd for C$_{32}$H$_{54}$ClNO$_4$: C, 69.60; H, 9.86; N, 2.54; Found: C, 65.76; H, 9.62; N, 2.63.

Antimelanoma Activity Assays

The relative efficacies of the prodrugs of betulinic acid and betulinic acid derivatives versus cancer cells can be established by determining the concentrations at which each prodrug inhibits the cancer cell activity to a predefined extent and then comparing the results. Typically, the preferred determination is the concentration that inhibits 50% of the activity in a biochemical assay, i.e., the 50% inhibitory concentration or "IC$_{50}$." IC$_{50}$ determinations can be accomplished using conventional techniques known in the art. In general, an IC$_{50}$ can be determined by measuring the activity of a given cell line in the presence of a range of concentrations of the compound under study. The experimentally obtained values of cell line activity then are plotted against the compound concentrations used. The concentration of the inhibitor that shows 50% cell line activity (as compared to the activity in the absence of any inhibitor) is taken as the IC$_{50}$ value.

The IC$_{50}$ values for the prodrugs of betulinic acid and betulinic acid derivatives were determined from concentration-response curves typically using concentrations ranging from 0.01 to 100 µg/mL. The IC$_{50}$ determinations can be accomplished by well-known methods in the art. An exemplary test method is as follows:

The cytotoxic potential of test compounds was determined with various cell lines as described previously in K. Likhitwitayawuid et al., *J. Nat. Prod.*, 56, pages 1468–1478 (1993). Briefly, various concentrations of test compounds (e.g., 0.1 to 100 µg/mL, dissolved in 10 L of 10% DMSO) were transferred to 96 well plates, and 190 L aliquots of cell suspensions (e.g., 5 10$^4$ cells/ml) were added to each well. The plates then were incubated for 72 hours at 37° C. (100% humidity with a 5% CO$_2$ atmosphere in air), and 100 L of cold 20% aqueous trichloroacetic acid was added to the growth medium in each well to fix the cells. The cultures were incubated at 4° C. for 30 minutes, washed, air dried, stained with sulforhodamine B solution, and washed with 1% acetic acid. Finally, 200 L of 10 mM Tris base was added to each well and the optical densities were determined at 515 nm utilizing an ELISA plate reader. In each case, a zero day control was performed by adding an equivalent number of cells to several wells and incubating at 37° C. for 30 minutes, and processing as described above. Optical density values obtained with the zero day control were subtracted, and cell survival, relative to control (solvent-treated) cultures, was calculated. Results were expressed as IC$_{50}$ values (i.e., concentration of test compound required to reduce cell number by 50%).

The derivatized betulinic acid prodrugs were tested against melanoma (Mel 2), and the in vitro results are summarized in the following table.

| | IC$_{50}$ (µg/mL) | |
|---|---|---|
| Compound | Mel 2 (10% DMSO)[a] | Mel 2 (Media)[b] |
| 27a | >20 | >20 |
| 27d | >20 | >20 |
| 27c | >20 | >20 |
| 27e | >20 | >20 |
| 27f | >20 | >20 |
| 4a | >20 | 9.6 |
| 4i | 5.0 | 4.0 |
| 4j | 3.0 | 1.9 |
| 4f | 3.3 | 2.7 |
| 28a | 1.6 | 2.8 |

[a]The test articles were dissolved in 10% DMSO.
[b]The test articles were dissolved in media.

To test the in vivo ability of betulinic acid to serve as an antineoplastic agent against malignant melanoma, a series of studies was performed with athymic (nude) mice injected subcutaneously with human melanoma cells (MEL-2). The initial study investigated the activity of betulinic acid against unestablished tumors. Treatment with betulinic acid began on day 1, i.e., 24 hours, following tumor cell injection. At doses of 50, 250, and 500 mg/kg (milligram per kilogram) body weight, betulinic acid demonstrated effective inhibition of tumor growth with p values of 0.001 for each dose versus a control.

In particular, the data was derived from experiments wherein four week old athymic mice were injected subcutaneously in the right flank with 3.0×10$^8$ UISO MEL-2 cells. UISO MEL-2 is a cell line derived from metastatic melanoma from human pleural fluid. Drug treatment was initiated on the day following tumor cell injection and continued every fourth day for a total of six doses. Four control animals received 0.5 ml intraperitoneal (IP) of PVP control solution, while treated animals (4 per group) received 50, 250 or 500 mg/kg/dose IP betulinic acid/PVP in deionized H$_2$O. Betulinic acid was coprecipitated with PVP to increase solubility and bioavailability. The mice were weighed, and the tumors measured with a micrometer every other day throughout the study. All animals were sacrificed and autopsied on day 33, when the mean tumor volume in the control animals was approximately one cm$^3$.

There was greater inhibition of tumor growth at the highest dose of betulinic acid versus the lowest dose (p=0.04). Toxicity was not associated with the betulinic acid treatment because toxicity is indicated by loss of body weight or other forms of acute toxicity. No weight loss was observed.

Next, in vivo testing of betulinic acid was performed on established melanomas. In this study, treatment was withheld until day 13, by which time a palpable tumor mass was present in all mice. Under these conditions betulinic acid successfully abrogated tumor growth (p=0.0001). Furthermore, tumor growth did not parallel that of the control (untreated) group even 14 days after the termination of treatment.

In particular, four-week-old athymic mice were injected with $5 \times 10^8$ MEL-2 cells subcutaneously in the right flank. Four treatment groups of five mice each were studied. In one group, the mice received 250 mg/kg/dose of IP betulinic acid/PVP every third day for six total doses initiated the day following tumor cell injection. The control group received 0.5 ml IP saline. A DTIC treatment group received 4 mg/kg/dose IP DTIC every third day from day 13 to day 28 of the study. The betulinic acid treatment group received 250 mg/kg/dose IP betulinic acid/PVP every third day from day 13 to day 27. The control and DTIC-treated mice were sacrificed and autopsied on day 36 due to their large tumor burden. The remaining mice were sacrificed and autopsied on day 41.

The efficacy of betulinic acid also was compared to DTIC, which is clinically available for the treatment of metastatic melanoma. The dose of DTIC, which is limited by toxicity, was selected to be equivalent to that administered to human patients. Tumor growth in the betulinic acid-treated group was significantly less than that observed in the DTIC-treated animals (p=0.0001). Compared to controls, DTIC produced a significant, but less pronounced, reduction in tumor growth, with a p value of 0.01. A fourth group in this study was treated with a schedule similar to that in the initial study. Under these conditions, betulinic acid, as demonstrated before, significantly inhibited tumor development (p=0.0001) and caused a prolonged reduction in tumor growth of up to three weeks following treatment termination.

Betulinic acid also showed activity against MEL-1 cells. In particular, four-week-old athymic mice were injected subcutaneously in the right flank with $5.0 \times 10^8$ UISO MEL-1 cells. Drug treatment was initiated on the day following tumor cell injection and continued every fourth day for a total of six doses. Four control animals received 0.5 ml intraperitoneal (IP) saline, while treated animals (4 per group) received 5, 50 or 250 mg/kg/-dose IP betulinic acid/PVP in dd $H_2O$. The mice were weighed, and tumors were measured with a micrometer every third day throughout the study. Treated animals were sacrificed and autopsied on day 41, when the mean tumor volume in the control mice was approximately 0.5 $cm^3$. The control mice then received six doses of 50 mg/kg every fourth day beginning day 41 and were sacrificed and autopsied on day 71.

The results with respect to MEL-1 cells were similar to the results with respect to MEL-2 cells. Betulinic acid therefore is active both against MEL-1 and MEL-2 cells. See, Pezzuto et al. U.S. Pat. No. 5,962,527, incorporated herein by reference, for additional information with respect to the in vivo activity of betulinic acid and derivatives against melanoma, and for in vivo activity against other forms of cancer.

Taking into account a unique in vitro cytotoxicity profile, a significant in vivo activity, and mode of action, betulinic acid is an exceptionally attractive compound for treating human melanoma. Betulinic acid also is relatively innocuous toxicitywise, as evidenced by repeatedly administering 500 mg/kg doses of betulinic acid without causing acute signs of toxicity or a decrease in body weight. Betulinic acid was previously found to be inactive in a Hippocratic screen at 200 and 400 mg/kg doses.

In particular, betulinic acid derivatives have been synthesized and evaluated biologically to illustrate that betulinic acid and betulinic acid derivatives possess selective antitumor activity against human melanoma cells lines in vitro. It has been demonstrated that modifying the parent structure of betulinic acid and betulinic acid derivatives provide numerous prodrugs that can be easily formulated and administered to an individual, which release betulinic acid or a betulinic acid derivative and used to prevent or inhibit malignant tumor growth, especially with respect to human melanoma. The antitumor activity of betulinic acid and betulinic acid derivatives is important therapeutically because these compounds exhibit a high activity against melanomas, but the compounds also possess a low water solubility. The low water solubility of betulinic acid and derivatives, however, can be overcome by providing an appropriate prodrug of betulinic acid or a betulinic acid derivative.

The above synthetic schemes show that modifying the betulinic acid and betulinic acid derivatives can provide prodrugs capable of releasing betulinic acid or a betulinic acid derivative in vivo. The prodrugs, therefore, can be used as potent antitumor drugs against melanoma and other cancers. The preparation of a prodrug overcomes the low solubility of betulinic acid and betulinic acid derivatives in water.

It is envisioned, therefore, that prodrugs of betulinic acid and betulinic acid derivatives are useful in the treatment of various cancers, for example, melanoma, a squamous tumor, a breast cancer, a colon cancer, a sarcoma, a human oral epidermoid carcinoma, a prostate cancer, a lung cancer, a glioma, or a neuroblastoma. Thus, the present invention concerns the use of prodrugs of betulinic acid and betulinic acid derivatives, or a pharmaceutical composition containing such an entity, for the manufacture of a medicament for the curative or prophylactic treatment of a cancer in a mammal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a prodrug of betulinic acid or a betulinic acid derivative" can be administered as the neat compound, or as a pharmaceutical composition containing such an entity.

In a further aspect, the present invention provides a method of treating a cancer in a human or nonhuman animal body which comprises administering to said body a therapeutically effective amount of a prodrug of betulinic acid or a betulinic acid derivative.

The prodrugs of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Compounds and pharmaceutical compositions suitable for use in the present invention include those wherein the prodrug is administered in an effective amount to achieve its intended purpose. More specifically, a "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the prodrug that results in achieving the desired effect. Toxicity and therapeutic efficacy of the prodrugs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the particular disease being treated and the patient's condition. Dosage amount and interval can be adjusted individually to provide plasma levels of the active moiety which are sufficient to maintain the therapeutic effects.

The amount of prodrug administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, dosage of the prodrugs of the present invention generally are about 0.5 to about 1000 mg daily for an average adult patient (70 kg). Thus, for a typical adult patient, individual tablets or capsules contain 0.2 to 500 mg of prodrug, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a prodrug of the present invention can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the prodrugs into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a prodrug of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% prodrug of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a prodrug of the present invention, and preferably about 1 to about 50% of a compound of the present invention.

When a therapeutically effective amount of a prodrug of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a prodrug of the present invention with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The prodrugs can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the prodrugs in water-soluble form. Additionally, suspensions of the prodrugs can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Prodrugs of the present invention also can be formulated in rectal compositions, such as suppositories or retention enemas, e.g., containing conventional suppository bases. In addition to the formulations described previously, the prodrugs also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a prodrug of the present invention can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A prodrug also can be injected parenterally, for example, intravenously, intramuscularly, subcutaneously, or intracoronarily. For parenteral administration, the prodrug is best used in the form of a sterile aqueous solution which can contain other substances, for example, salts, or monosaccharides, such as mannitol or glucose, to make the solution isotonic with blood.

For veterinary use, a prodrug of the present invention or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a prodrug of the present invention, together with a pharmaceutically acceptable diluent or carrier therefor. There is further provided by the present invention a process of preparing a pharmaceutical composition comprising mixing a prodrug of the present invention, together with a pharmaceutically acceptable diluent or carrier therefor.

In a particular embodiment, the invention includes a pharmaceutical composition for the curative or prophylactic treatment of a cancer in a mammal, including humans, comprising prodrug of the present invention, together with a pharmaceutically acceptable diluent or carrier.

What is claimed is:

1. A compound having a formula

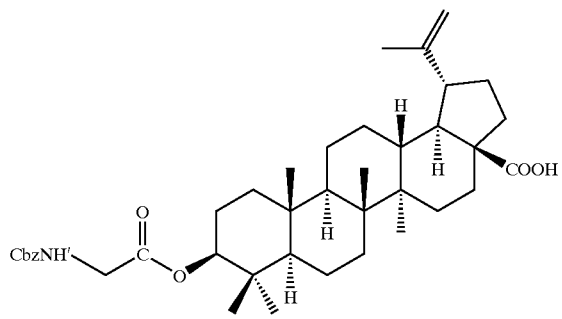

or salts thereof.

2. A pharmaceutical composition comprising a compound of claim 1 and a pharmaceutically acceptable carrier.

3. A method of treating a cancer sensitive to a betulinic acid derivative comprising administering to an individual in need thereof a therapeutically effective amount of a compound of claim 1.

4. The method of claim 3 wherein the cancer is selected from the group consisting of a melanoma, a squamous tumor, a breast cancer, a colon cancer, a sarcoma, a human oral epidermal carcinoma, a hormone-dependent breast cancer, a prostate cancer, a lung cancer, a glioma, a melanoma, and a neuroblastoma.

5. A method of treating a cancer sensitive to a betulinic acid derivative comprising administering to an individual in need thereof a therapeutically effective amount of a composition comprising a compound of claim 1 and a carrier.

6. A method of treating HIV comprising administering to an individual in need thereof a therapeutically effective amount of a compound of claim 1.

7. A method of treating HIV comprising administering to an individual in need thereof a therapeutically effective amount of a composition comprising a compound of claim 1 and a carrier.

* * * * *

UNITED STATES PATENT AND TRADEMARK OFFICE
CERTIFICATE OF CORRECTION

PATENT NO.         : 6,569,842 B2
APPLICATION NO. : 09/930656
DATED              : May 27, 2003
INVENTOR(S)        : John M. Pezzuto et al.

It is certified that error appears in the above-identified patent and that said Letters Patent is hereby corrected as shown below:

At column 1, line 5, insert --This invention was made with Government support under contract CA 52956 awarded by the National Institutes of Health. The Government has certain rights in this invention.--

Signed and Sealed this

Twenty-fifth Day of March, 2008

JON W. DUDAS
*Director of the United States Patent and Trademark Office*